United States Patent [19]
Herweck et al.

[11] Patent Number: 5,411,550
[45] Date of Patent: May 2, 1995

[54] IMPLANTABLE PROSTHETIC DEVICE FOR THE DELIVERY OF A BIOACTIVE MATERIAL

[75] Inventors: Steve A. Herweck, Nashua; Theodore Karwoski, Hollis; Paul Martakos, Pelham, all of N.H.

[73] Assignee: Atrium Medical Corporation, Hudson, N.H.

[21] Appl. No.: 109,103

[22] Filed: Aug. 19, 1993

Related U.S. Application Data

[63] Continuation of Ser. No. 760,753, Sep. 16, 1991, abandoned.

[51] Int. Cl.$^6$ .................... A61F 2/06; A61F 2/04
[52] U.S. Cl. .......................... 623/1; 623/1.2; 600/36
[58] Field of Search ................ 623/1, 11, 12; 606/191–200; 600/36; 138/117, 118.1

[56] References Cited

U.S. PATENT DOCUMENTS

| | | | |
|---|---|---|---|
| 4,550,447 | 11/1985 | Seiler, Jr. et al. | 623/1 |
| 4,737,146 | 4/1988 | Amaki et al. | 604/51 |
| 4,749,585 | 6/1988 | Greco et al. | 427/2 |
| 4,776,337 | 10/1988 | Palmaz | 128/343 |
| 4,898,669 | 2/1990 | Tesio | 210/232 |
| 5,024,671 | 6/1991 | Tu et al. | 623/1 |

FOREIGN PATENT DOCUMENTS 1517957  10/1989  U.S.S.R. .................... 623/11

OTHER PUBLICATIONS

"Catheter Angiography Through Prosthetic Vascular Grafts Using a Teflon Sheath" vol. 148, No. 2; pp. 565; Radiology, vol. 148, Aug. 1983.

"Comparison of Normal Saline and Heparin Solutions for Maintenance of Arterial Catheter Patency;" Clifton et al.; Heart & Lung pp. 115–118; Mar. 1991 vol. 20, No. 2.

"New Methods of Drug Delivery;" Robert Langer; Science, vol. 249 Sep. 28, 1990 pp. 1527–1533.

"Catheterization of Synthetic Vascular Grafts;" Mohr et al.; Journal Vascular Surgery; vol. 3; No. 6; Jun. 1986 pp. 854–856.

"Safe and Effective Catheter Angiography Through Prosthetic Vascular Grafts;" Smith et al.; Radiology, vol. 138; Feb. 1981.

*Primary Examiner*—Randall L. Green
*Assistant Examiner*—Debra S. Brittingham
*Attorney, Agent, or Firm*—Lahive & Cockfield

[57] ABSTRACT

An implantable prosthetic device for sustained release of a bioactive material into a fluid flow pathway of a patient comprises a body adapted for attachment to the fluid flow pathway. The body defines a primary lumen for accommodating fluid flow therethrough and at least one secondary lumen at least a portion of which is separated from the primary lumen by a wall sufficiently permeable to permit a bioactive material disposed in the lumen to diffuse through the wall and into the primary lumen. The bioactive material can be either a therapeutic or diagnostic agent. In a particular embodiment of the invention, the device comprises a tubular body consisting of stretched and/or expanded polytetrafluoroethylene and is adapted for attachment to a blood vessel of a patient.

20 Claims, 4 Drawing Sheets

IMPLANTABLE PROSTHETIC DEVICE FOR THE DELIVERY OF A BIOACTIVE MATERIAL

This application is a continuation of application Ser. No. 07/760,753, filed Sep. 16, 1991, now abandoned.

BACKGROUND OF THE INVENTION

One type of implantable device is a synthetic vascular graft such as is commonly used to replace damaged or dysfunctional arterial or venous pathways, for example at the site of an aneurysm or occlusion. Bypass grafts are often used to divert blood flow around damaged regions to restore blood flow. Another use of vascular prostheses is for creating a bypass shunt between an artery and vein, specifically for multiple needle access, such as is required for hemodialysis treatments. Following multiple percutaneous invasions into a vein, the vein may either collapse along the puncture track or become aneurysmal, leaky or fill with clot, causing significant risk of pulmonary embolization. Vascular prostheses have been used for many years as an alternative to patients' own veins for vascular access during hemodialysis.

Materials research has led to the development of some synthetic materials for use in artificial vascular prostheses. For example, polytetrafluoroethylene (PTFE), a polymeric material which may be stretched to a specific length and expanded to a specific thickness, is often used to fabricate single lumen artificial veins and arteries. Typically, however, PTFE vascular grafts cannot safely be used to withdraw blood until they have been in place in the body for a minimum of 14 days after surgery and have become surrounded by fibrotic tissue. This is because bleeding occurs at the site of a needle puncture in PTFE grafts if fibrotic tissue is absent. Complications which can result from early puncturing of PTFE arteriovenous fistulas include a hematoma surrounding the graft, false aneurysm, and graft occlusion.

Various other synthetic materials, in addition to PTFE, have been used for vascular grafts, including Dacron® brand and other synthetic polyester fibers, mandrel spun polyurethane, and silicon elastomer fibers. Additionally, vascular grafts have been formed using autologous saphenous vein, modified bovine carotid xenograft, and modified human umbilical vein. None, however, has overcome the problems associated with early failure of the graft following implantation.

In an effort to address these problems, various types of vascular access devices have been developed. One example of such a device is described by Tesio in U.S. Pat. No. 4,898,669 (Feb. 6, 1990). This device is a catheter system mechanically coupled with a prosthetic vascular graft for use in blood purification. Devices available for long-term, repeated vascular access allow a catheter to be introduced to a blood flow pathway, but they do not generally allow chronic, permanent implantation. In some cases, due to the materials used, an autoimmune response occurs resulting in the formation of an occlusive hematoma.

Another vascular graft is disclosed in U.S. Pat. No. 4,619,641 (Oct. 28, 1986) to Shanzer which discloses a coaxial double lumen device for use in hemoaccess. The space between the two lumina is filled with a self-sealing, non-biodegradable polymer which does not permit escaped bleeding following needle puncture. The Shanzer product consists of an outer tube positioned over an inner tube, both tubes being made of expanded PTFE.

While research has also led to the development of some improved drug delivery systems, these systems still require a significant amount of medication to achieve a therapeutic level for an organ specific function such as is required for a whole body systemic effect. Conventional drug delivery systems, for example, including orally applied tablets and liquids, injections, and localized intravenous infusions, all must be applied in rather large doses to achieve a systemic effect. Introduction of a catheter directly into a blood flow pathway, for example, results in delivery of bolus amounts of drug to a patient's system. This results in uncontrolled and often varied, whole body physiological effects, as well as blood vessel wall injury at the site of penetration. Much of the current research in drug delivery, therefore, has been directed to allowing delivery of drugs to a patient in a controlled, non-bolus manner, and in generally smaller doses. This requires that delivery be localized, or targeted, to a cell specific organ.

Presently, material research has also enabled modern developments such as transdermal and time-release delivery systems which also create a whole body systemic effect. Future research suggests the extended use of chemically modified drugs complexed to carrier or bioactive agents, organic vesicles, and controlled delivery systems such as micro-pumps and mini-pumps. These and other new drug delivery systems are discussed, for example, by R. Langer, In: "New Methods of Drug Delivery", *Science* 249:1527-1533 (Sep. 28, 1990).

Additionally, recently published evidence indicating that cellular activities are controlled by receptors, "molecular switches" on the membrane surface of cells suggests that bioactive and pharmaceutical drug interactions, whether initiators or inhibitors, can be utilized to improve implantable organ and autogenous organ transplant performance. These receptors control cellular activities by binding with highly specific substances referred to as "ligands." Like the action of a key in a lock, ligands fit into receptors and, if the fit is precise, turn on or off certain cellular processes. Some ligands act as antagonists to inhibit cellular activities by blocking a receptor. Research has shown that many aspects of cardiovascular disease are controlled by specific cell surface receptors.

SUMMARY OF THE INVENTION

The invention features an implantable, biocompatible prosthetic device for the sustained release of a drug or other bioactive material directly into a blood or other body fluid flow path. The device is a polymeric bi- or multilumenal tubular article which can be attached, for example, to an artery or vein to form a vascular graft or shunt. The device can also be used to provide organ to organ fluid communication. The device contains a primary lumen, which is dedicated to the flow of blood or other body fluid and at least one secondary lumen. The lumina are separated by a microporous, semi-permeable wall which permits passage of an agent from the secondary lumen to the primary lumen. Additionally, the microporosity of the separating wall promotes the growth, motility, and/or migration of cells into and through the wall.

The secondary lumen is particularly well suited to contain a material, such as a drug or other bioactive agent, which permeates the porous wall between the secondary lumen and the primary lumen over a sustained period of time. The rate at which the drug or other agent penetrates the porous wall is determined by several factors, including the size and number of the pores and the size of the drug molecule.

In one embodiment of the invention, the prosthetic device comprises a tube which is adapted for attachment to a blood flow pathway, and for conducting the flow of blood therethrough. The tube has a biocompatible or bioinert exterior surface, and defines a primary lumen axially extending along the length of the tube, and at least one additional or secondary lumen. The secondary lumen is separated from the first lumen by a microporous wall which allows a drug introduced into the secondary lumen to diffuse across the wall and into the primary lumen, and thus directly into the blood flow pathway. This is caused by patient cells penetrating the exterior wall of the tube and displacing air contained in the micropores of the tube's microporous structure. The displaced air, in turn, displaces material contained in the secondary lumen forcing the material to diffuse into the primary lumen.

The secondary lumina can be pre-filled with a selected drug which time-diffuses or otherwise perfuses across the membrane. The lumina can also be filled with drug-producing cells which disperse a drug product into the secondary lumina, from which it then diffuses, as discussed above, into the primary lumen. The primary lumen and/or the secondary lumina can also be seeded with cells, for example endothelial cells, which proliferate at the site of attachment due to the cell to cell contact afforded through the walls of the microporous structure. The invention allows the endothelial cells to thrive, therefore, which helps to prevent undesired occlusion of the graft.

In another embodiment of the invention, the tube features an external drug delivery device attached thereto by a second tube or catheter. The catheter is connected to the secondary lumen. The delivery device injects the drug into the secondary lumen from an external source. The device can be any of a variety of commercially and technologically available systems, such as, for example, a biologically activated mini-pump which is either subcutaneously or extracutaneously located, or an external mechanical pump.

The present prosthetic device is preferably made from stretched and expanded polytetrafluoroethylene (PTFE). Stretched and expanded PTFE contains a porous network of nodes and fibrils which are created during the stretching and expansion process of porous tubing from PTFE. This porous network provides a semi-permeable wall or membrane between the lumina of the device.

In another aspect, the invention features a method for delivering directly into a fluid flow pathway in a controlled manner a bioactive material, such as a prophylactic or therapeutic drug, or a diagnostic material, such as a radiolabeled antibody. One embodiment of this aspect of the invention includes the steps of pre-filling one of the secondary lumina of the above-described implantable device with a bioactive material and implanting the device in a fluid flow pathway such as a vein or artery. In this manner, fluid flow is established through the primary lumen of the device. The pre-filled material diffuses across the wall or membrane separating the secondary lumina from the primary lumen in a controlled manner, thereby delivering the drug directly into the fluid, blood or otherwise, flowing through the primary lumen.

In another embodiment of this aspect of the invention, a separate external drug delivery system is attached to at least one of the secondary lumina. This allows transport of the drug into the secondary lumen from an external source. The drug then diffuses across the interluminal wall as described above.

The invention has several advantages. It allows implantable vascular grafting and controlled and/or continuous drug delivery to be combined. Additionally, the invention allows a bioactive substance to be delivered directly into a patient's bloodstream at a controlled rate without using intravenous injection, which generally must be performed in a hospital or doctor's office. The device and method allow a bioactive substance to be injected into the secondary lumen all at once from an external source, then released into the patient's bloodstream at a slower, continuous rate as the substance passes from the secondary lumen into the primary lumen of the graft. This sustained release of a substance into the bloodstream over time is less likely than known drug delivery methods to result in distal embolization. The graft provides a site for repeated cannulation which does not require directly accessing the bloodstream and therefore reduces the incidence of bleeding at the injection site.

BRIEF DESCRIPTION OF THE DRAWINGS

The foregoing and other objects of this invention, the various features thereof, as well as the invention itself, may be more fully understood from the following detailed description, when read together with the accompanying drawings, in which.

Like reference characters in the respective figures indicate corresponding parts.

DETAILED DESCRIPTION OF THE INVENTION

In its broadest aspect, the invention features a multilumenal prosthetic device for implantation into a patient. The invention can be utilized, for example, as a vascular graft providing sustained release of a selected bioactive agent or diagnostic material directly into a blood or other fluid flow pathway. The device has at least two lumina which are separated by a porous, semipermeable wall. In the case of the device being used as a vascular graft, it is grafted onto a vein or artery in an individual such that the primary lumen becomes part of the individual's blood flow pathway. The secondary lumen is filled with a material such as, for example, a bioactive or diagnostic agent and the porous wall between the lumina allows the material disposed in the secondary lumen to diffuse into the bloodstream flowing through the primary lumen. As described in further detail below, the device allows the release of the material across the wall or membrane into the bloodflow pathway in a controlled manner.

The device comprises a main, or primary lumen, which is of a diameter sufficient to allow blood flow appropriate for the artery or vein to which it is attached to occur. Thus, the device has the geometric configuration of a tube, open at least at one end, and typically at both ends. The open end is sutured to an opening in the patient's arteriovenous pathway, thus becoming an extension of that pathway.

The device also contains at least one secondary lumen adjacent to the first lumen. At least one of the secondary lumina contains or is adapted to contain the selected bioactive or diagnostic materials. These materials can include, for example, therapeutic or prophylactic agents, such as a drug, protein, enzyme, antibody or other agent, or cells which produce a drug, protein, enzyme, antibody, or other agent. The diagnostic material can include, for example, a radiolabeled antibody or antigen.

In one embodiment of the invention, one or more of the secondary lumina are pre-filled with the bioactive material. For example, the pre-filled secondary lumen can contain cells which secrete a bioactive agent. As a variation of this embodiment, another embodiment may include a pre-filled lumen in conjunction with other secondary lumina into which drugs or diagnostic materials are introduced after implantation.

Figure 1A:
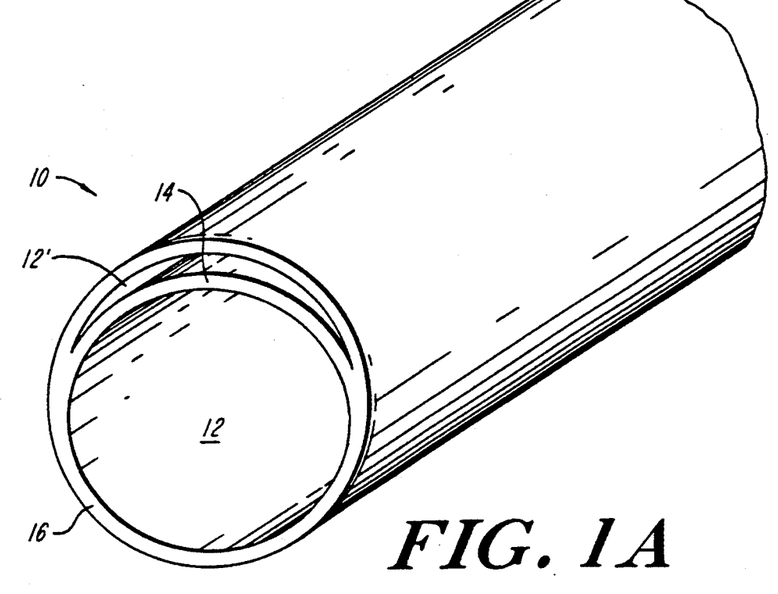
FIG. 1A is a schematic perspective view of a biluminal vascular prosthesis of the present invention.

Specific embodiments of the device are illustrated by the Figures. FIG. 1A shows a bilumenal tubular structure 10 having a first lumen 12 and a secondary lumen 12'. The first lumen 12 has a structure sufficient for blood flow therethrough. For a vascular graft, the diameter of this lumen 12 is generally the same or similar in size to the host artery or vein to which it is grafted. As mentioned, however, the structure 10 can be formed to accommodate other types of fluid flow.

Figure 1B:
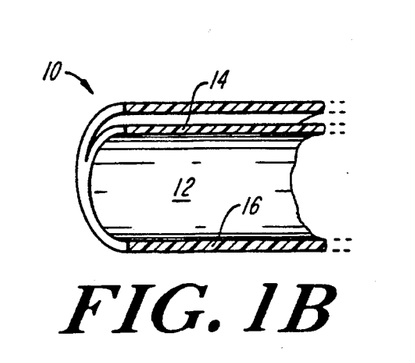
FIG. 1B is a schematic longitudinal cross-sectional view of the embodiment of FIG. 1A.

As shown in FIG. 1B, the secondary lumen 12' is adjacent the first lumen 12, and is separated by a semipermeable, micro-porous, wall 14. The wall 14 has a permeability sufficient to allow diffusion of the bioactive agents or diagnostic material of choice from the secondary lumen 12' into the fluid flow pathway defined by the first lumen 12. In a multi-lumen arrangement, i.e., a device having more than two lumina, the adjoining wall 14 lies in communication between each of the secondary lumina and the primary lumen. Alternatively, there can be a semi-permeable wall between each secondary lumen 12' and the first lumen 12, with an impermeable wall among the secondary lumina.

The thickness and permeability of the wall 14 can be adapted to accommodate different drugs, bioactive or bioinert agents, and the like, and to control the rate at which the material disposed in the secondary lumina 12' diffuses across the wall 14. Control over the release of the drug or agent can be obtained by choosing appropriate molecular weights, degrees of crystallinity and/or expansion parameters in the polymer matrix forming the structure 10. The wall 14 can be manufactured having a predetermined permeability factor, and the concentration of materials to be transported across the membrane can be selected accordingly.

The opportunity to control the permeability of the wall 14 is afforded during the extrusion and expansion process as discussed in greater detail below. By controlling the internodal distance of the polymeric matrix and properly selecting the specific resin composition and expansion conditions, the porosity of the wall 14 can be determined.

The outer diameter (OD) of the external wall of the structure 10 is generally in the range of from about 3 mm to about 30 mm. The internal diameter (ID) of the primary lumen is generally from about 1 mm to about 28 mm depending upon the type of blood flow through the prosthesis. The OD and ID vary according to the type of pathway for which the prosthesis is used. For example, arterial prostheses will generally have OD of from about 6 mm to about 18 mm, whereas venous prostheses will generally have an OD of from about 12 mm to about 24 mm. The ID of the secondary lumina 12' is generally from about 0.1 mm to about 6 mm, depending upon the OD.

Figure 1C:
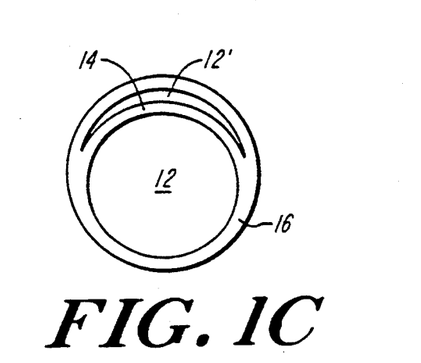
FIG. 1C, 1D and 1E show schematic cross-sectional views of alternative configurations of the biluminal device of FIG. 1A.
Figure 1D:
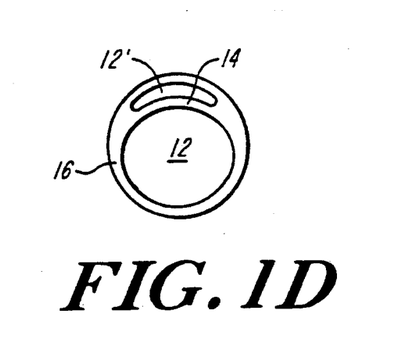
Figure 1E:
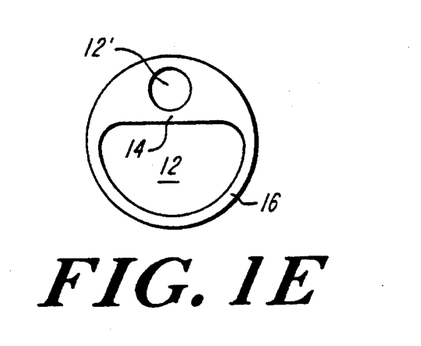

As shown in FIGS. 1C, 1D, and 1E, the cross-sectional configuration of the lumina designed in accordance with the invention can vary in size and shape depending upon the specific application. In FIG. 1C, the secondary lumen 12' extends over approximately one-third of the circumference of the lumen 12. FIG. 1D shows a diminished relative size of the secondary lumen 12' with respect to the first lumen 12, and FIG. 1E shows a first lumen 12 having an adjacent secondary lumen 12' of dimensions sufficient only to transport substances of a few microns in size. The relative size of the secondary lumen 12' depends on the type of substance to be transported through secondary lumen 12', and the desired rate of diffusion across wall 14. The permeability of wall 14 may be a factor in determining the appropriate size of secondary lumen 12'.

In another aspect, the invention features a method for delivering a bioactive agent or diagnostic material directly to a patient's body fluid, bloodstream or otherwise, in a controlled manner. In the method, a surgeon or other qualified person, surgically exposes the desired region of the patient for introduction of the prosthetic device 10. The desired site may, for example, be an area of occlusion or weakness in the patient's arteriovascular system. In such a case, during interruption of the patient's blood flow the prosthesis 10 is surgically implanted and sutured or otherwise secured in place. Proper positioning of the prosthesis 10 requires alignment of the primary lumen 12 with the blood flow pathway such that the blood flow is diverted through the primary lumen 12. The secondary lumen 12' either contains or is filled with a drug or agent of choice. The drug or agent perfuses across the interluminal wall 14 into the bloodstream at a controlled and substantially continuous rate. In this manner, the present invention allows continuous administration of the drug over a prolonged period of time similarly to controlled release systems which deliver a drug at a predetermined rate over a definite period of time.

In an example of use of the present invention, an antibody which is specific to a protein indicative of the presence of malignancy is introduced into the vascular system of a patient utilizing the present device and method. The device 10 is surgically implanted in a patient's vascular system and blood flow is established through the primary lumen 12. The antibody is added to the secondary lumen 12' either before implantation by pre-filling the lumen or after implantation by injecting the antibody composition into the secondary lumen. The antibody is labelled, for example, with a remotely detectable radioisotope such as $125_I$. The labelled antibody moves across the porous wall 14 between the primary lumen 12 and the secondary lumina 12' into the patient's blood flow pathway, which flows through the primary lumen 12. Once in the pathway, the labelled antibodies travel to the site of the malignancy and bind at the appropriate protein binding sites. The concentration of the radioisotope at the target site can then be detected using an appropriate detection device, e.g., a gamma camera. Additional doses of the antibody composition can be injected into the secondary lumen 12' through a cannula, or through a pre-attached catheter which communicates with the secondary lumen 12', without directly invading the patient's bloodstream.

In another exemplary use of the present invention, combinations of anti-coagulant platelets and plasminogen activators, such as heparin, hirudin and tPA can be injected into the secondary lumen 12' to be released at a controlled, continuous, rate into the bloodstream. Continuous release of a solution containing either heparin, tPA, or combinations of the two into a vascular graft area has been shown to be effective in reducing occlusion from intimal hyperplasia, while not resulting in whole body systemic anti-coagulation. Clifton et al., *Heart & Lung*, 199(1): 115-118 (March, 1991).

In another example of use of the invention, the prosthesis 10 can be used for distribution of chemotherapy agents which are often very toxic and often cause arterial and venous blood vessel destruction at the needle catheter entry site. A major complication of such chemotherapy is the constant risk of permanent, significant delivery site complications such as infection or occlusion due to thrombus formation at the vessel wall injury. The high concentration of such toxic agents very often has a deleterious effect on the blood vessel, further complicating the healing required for the needle tract or catheter injury incurred at the site of drug infusion.

The device 10 eliminates such needle and catheter injury to the blood vessel and large bolus chemical exposure to the native vessel with these highly toxic chemotherapy agents. Moreover, the device 10 can be replaced if long term therapy causes eventual failure or thrombus occlusion. A vein or artery permanently destroyed by chronic therapy, on the other hand, is irreplaceable. Similar problems and corresponding solutions also exist for hemodialysis patients whose native veins are consumed by repetitive needle penetration and permanent blood vessel wall injury.

The tube structures of the invention can be manufactured from any suitable biocompatible material that can be arranged to form a microporous structure. Polymeric materials which are useful for this purpose include, for example, either expanded or unexpanded polytetrafluoroethylene (PTFE), Dacron ® brand polyester, and other synthetic polyester fibers such as mandrel spun polyurethane and silicone elastomeric fibers. Also, copolymeric materials such as described in U.S. Pat. Nos. 4,187,390 and 4,973,609 can be utilized. These are materials made up of more than one type of monomer and have advantages as described in the cited patents, in some applications. The structures can also be formed by extrusion, form molding, or weaving using techniques well known in the art.

In a preferred embodiment, the inventive prosthesis is manufactured by paste forming and rapidly stretching and/or expanding highly crystalline, unsintered, polytetrafluoroethylene. Paste forming by extrusion of PTFE is well-known in the art. Generally, the steps in paste-forming include mixing the resin with a lubricant, such as odorless mineral spirits, and then forming the resin by extrusion into shaped articles. The lubricant is removed from the extruded article by drying, following which the article is sintered by its being heated above its crystalline melting point of approximately 327° C. The sintered, unexpanded, article is a relatively impermeable product. To achieve a greater degree of permeability in the finished product, however, the prostheses of the invention can be formed from an unsintered resin.

Paste-formed, dried, unsintered, shapes can be further treated by expanding and/or stretching them in one or more directions under certain conditions so that they become porous yet retain their strength. Such stretching and expansion with increased strength occurs with certain preferred tetrafluoroethylene resins, e.g., PTFE. The porosity of the material is affected by the temperature and rate at which it is stretched and expanded. A method for manufacturing porous PTFE tubing appropriate for use in the present invention is described in detail, for example, in U.S. Pat. Nos. 3,953,566 and 4,973,609 the teachings of both of which are hereby incorporated by reference herein.

Stretched and expanded PTFE is characterized by a microstructure of nodes interconnected by small fibrils. The space between the nodes and the number of fibrils is controlled by changes in the temperature and rate of stretching and expansion of the PTFE, to produce tubing having predetermined porosity and flex qualities. For example, products which are stretched and expanded at high temperatures and high rates have a more homogeneous structure, i.e., they have smaller, more closely spaced nodes, which nodes are interconnected with a greater number of fibrils. While the resulting structure is stronger than products stretched and expanded at lower temperatures and rates, the porosity is also reduced. Thus, by controlling these two factors, it is possible to construct a series of tube structures having a range of porosity within a desirable range of strength.

The tube structures of the invention can be formed using other paste-forming operations known to those skilled in the art, for example, any of the available molding processes. Resins other than PTFE may also be used which are generally formable into such tube structures, and which may result in relatively fluid impermeable structures.

The prosthesis 10 can be coated on both the interior luminal and/or the exterior surfaces with a biocompatible material to render it more hydrophilic or hydrophobic, or to allow specific protein binding or attachment after implantation. Coating materials which are useful for this purpose include, for example, various glycoproteins, albumin or polymeric coatings often used for plasma polymerization, and solvable polymeric coatings such as EVA and PVA Due to the physiological properties of both the arterial and venous system, however, it is important for the prostheses 10 to be gas permeable, or selectively gas permeable, to permit oxygen-carbon dioxide exchange. However, even gas impermeable tube structures may be useful as vascular grafts in certain anatomical applications.

Figure 2:
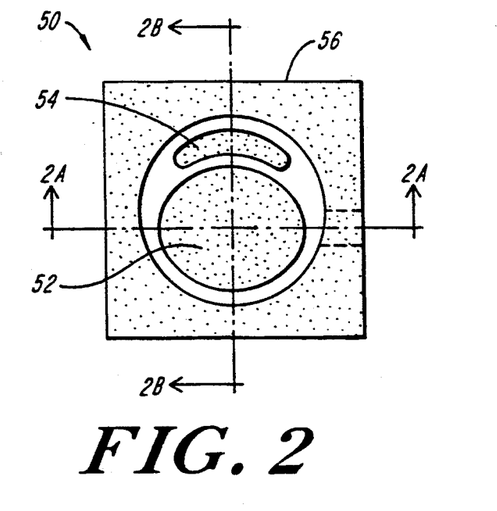
FIG. 2 shows a schematic front elevation view of a die used in the manufacture of the biluminal device of FIG. 1A.

As stated, in the preferred embodiment, the prostheses of the present invention are formed by extrusion of PTFE which is performed using dies of predetermined shape of the type known in the art. FIGS. 1C through 1E, for example, show cross-sectional views of prostheses of the invention made using different exemplary dies. In particular, FIG. 2 schematically shows an exemplary die 50, corresponding to the illustrated prosthesis of FIG. 1A. The dies are manufactured from materials and according to methods which are well known in the art.

Figure 2A:
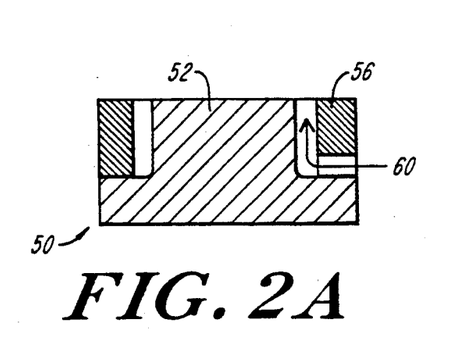
FIG. 2A and 2B show schematic cross-sectional views of the die of FIG. 2 taken along planes A—A an B—B, respectively.
Figure 2B:
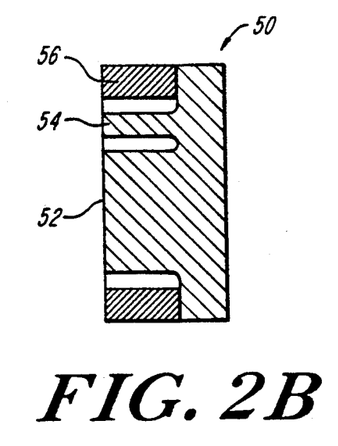

Generally, and as is illustrated in FIG. 2, the die 50 consists of a peripheral support structure 56 encasing a first solid die-piece 52 for forming a first lumen, and a second solid die-piece 54 proximal to the first die-piece 52 for forming a secondary lumen. The specific spacing of the first die-piece 52 from the second die-piece 54 depends on the specific desired prosthesis configuration. As best shown in cross-section in FIG. 2A, the die 50 may include an external port 60 for introduction of PTFE paste or the like for extrusion. FIG. 2B shows in cross-section the exemplary die 50 of FIG. 2, showing aperture 58 for forming membrane (14 of FIG. 1) of the invention.

After the PTFE resin is formed, such as by extrusion as discussed above, it is stretched and/or expanded and then sintered while being held in the stretched and/or expanded state. Stretching refers to elongation of formed resin while expansion refers to enlargement of the formed resin perpendicularly to its longitudinal axis. The rate of stretching and the stretch ratio affect the porosity of the finished product in a predictable manner allowing a prosthetic device to be produced having a specified porosity. The rate of stretching refers to the percentage of elongation per second that the resin is stretched while the stretch ratio refers to the relationship between the final length of the stretched resin and the initial length of the stretched resin. For example, stretching an extruded PTFE tube at a stretch ratio of two to one and a stretch rate of sixty results in a porosity of approximately forty. This porosity is unitless and is determined as set forth on page eighty-four of the American Society For Testing of Materials' Special Technical Publication Number 898. So, for example, based on stretch ratios ranging from two to one, to six to one, a stretch rate of sixty percent per second yields a porosity of between approximately forty and approximately ninety, a stretch rate of one hundred and forty percent per second yields a porosity of between approximately sixty and approximately eighty-five, and a stretch rate of nine hundred percent per second yields a porosity of between approximately sixty-five and approximately eighty-five.

In addition to the porosity, the geometry of the node and fibril network of PTFE can be controlled during stretching and expansion. In the case of uniaxial stretching, that is, elongation of the formed PTFE resin along the direction of extrusion, the nodes are elongated causing the longer axis of each node to be oriented perpendicularly to the direction of stretch. Accordingly, the fibrils are oriented parallel to the direction of stretch. Axial stretching, additionally includes expanding the PTFE resin in the radial direction and can be utilized to produce a prosthetic device having a composite porosity. As in uniaxial stretching, the rate and ratio of radial expansion affects the resulting porosity of the prosthetic device.

In one embodiment, the apparatus of the present invention includes co-extruded plural lumina, the secondary lumina 12' of which extend substantially along the entire length of the first lumen 12. In another embodiment of the invention, however, as illustrated in FIG. 3, the secondary lumen 12' extends along only a portion of the first lumen 12.

Figure 3:
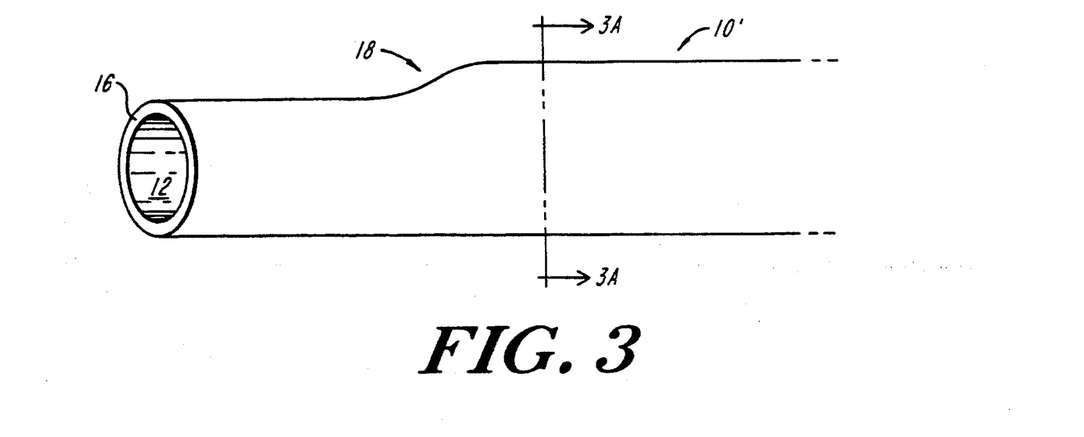
FIG. 3 is a schematic side elevation view of a bilumenal device in which the secondary lumen is partially co-extensive with the primary lumen.
Figure 3A:
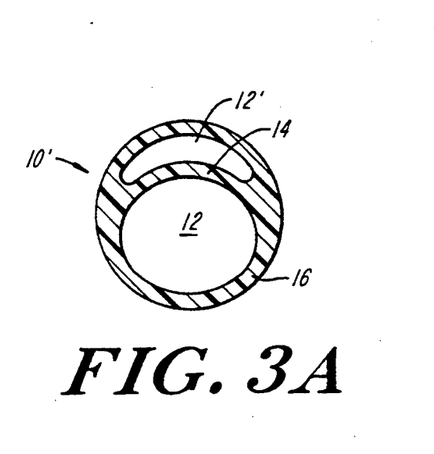
FIG. 3A is a schematic cross-sectional view of the embodiment of FIG. 3.

The illustrated prosthesis 10' of FIG. 3 is structurally similar to the prostheses 10 described above. As shown in cross-section FIG. 3A, the portion of the prosthesis 10' which includes a secondary lumen comprises a microporous, semi-permeable, wall 14 separating the secondary lumen 12' with the first lumen 12. However, in this illustrated embodiment, the secondary lumen only extends along a predetermined portion of the prosthesis 10'.

The embodiment shown in FIG. 3 may be manufactured in a manner similar to that described above. The extrusion die for forming the partially-extending lumen may be modified in a manner known to those skilled in the art. For example, the die used in the extrusion of this embodiment of the invention may include a gate-type device which enables selective opening and closing of an aperture to coextrude a secondary lumen.

Figure 4:
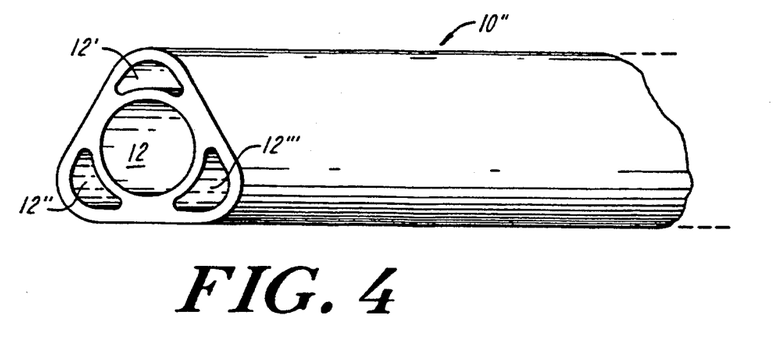
FIG. 4 is a schematic perspective view of a multilumenal device of the invention.

An alternative embodiment of the prosthesis of the present invention is illustrated in FIG. 4. In the illustrated prosthesis 10', the first lumen 12 is essentially round, with the secondary lumen 12' forming a polygonal configuration around the first lumen 12. While this illustrated embodiment shows three secondary lumen 12°, other forms of the invention may include fewer or more secondary lumina. In addition, the apparatus of the invention may have various overall geometric configurations, depending upon the anatomical destination of the prosthesis 10'.

An important aspect of the invention is the introduction of a bioactive agent, pharmaceutical, chemotherapy agent or diagnostic material into a secondary lumen for perfusion into the blood flow pathway of the patient as it is channeled through the first lumen of the prosthesis. This introduction of material may occur by including a mini-pump attached to the secondary lumen of the prosthesis, for example, by a catheter.

Figure 5:
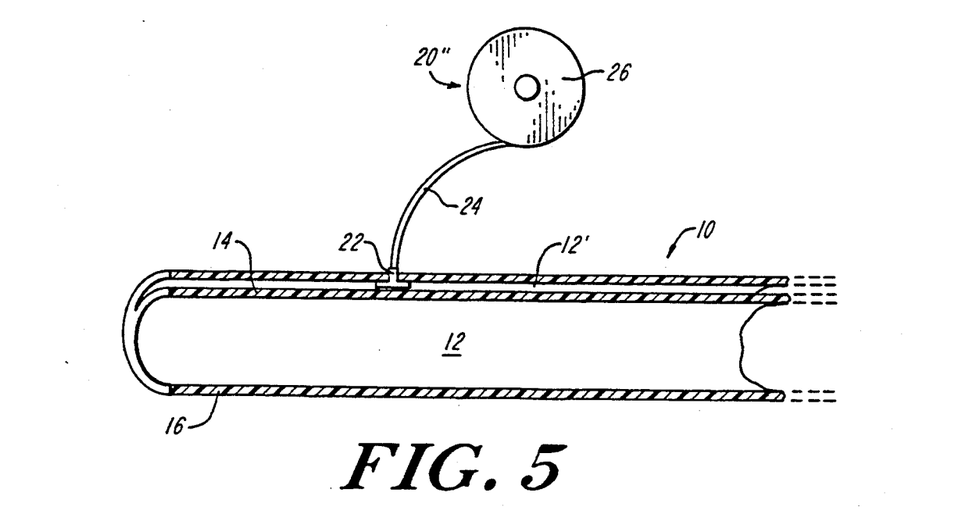
FIG. 5 is a schematic longitudinal cross-sectional view of an embodiment of the invention having a preattached mini-pump.

As shown in FIG. 5, a mini-pump 20 may be placed in communication with at least one of the secondary lumen 12' for perfusion of a drug into the secondary lumen 12'. The mini-pump 20 can be used to deliver a predetermined amount of a drug at a preselected rate to the secondary lumen 12. Thereafter, the drug perfuses across the microporous, semi-permeable, wall 14 and into the bloodflow pathway of the first lumen 12. Mini-pumps which may be used with the prosthesis of the invention are commercially available. Some examples are Alza Pump, Thermedics' Infusaid Pump, Medtronic's Infusable Pump, and INFU.DISKS ™ (Electrochemical Drug Delivery, Inc. San Diego, Calif.) designed for subcutaneous delivery of drugs or diagnostic agents. The mini-pump 20 may be located externally to the patient, or may be surgically subcutaneously implanted.

As shown in FIG. 5, the mini-pump 20 contains a drug reservoir 26 from which a connector tube 24 extends. The connector tube 24 may either be integral with the reservoir 26, or mechanically, detachably connected to the reservoir 26. The connector tube 24 extends from the reservoir 26 to a secondary lumen 12' of a prosthesis 10. The connector tube 24 may connect to the secondary lumen 12' by means of a mechanical attachment device 22, as illustrated, or may be formed integral with the secondary lumen 12'. Mechanical attachment devices are well known in the art, and include luer-locks. It is generally preferable that the mechanical attachment device is such that the mini-pump may readily be replaceable, thus attachment devices which do not require the application of pressure are preferable over pressure-lock devices.

Similarly, a mechanical pump, infusion system, or other drug delivery system located outside the host body may be attached for the delivery of a drug or other bioactive material into a secondary lumen. The drug delivery source may either be integral with the secondary lumen, or may be mechanically, releasably attached.

Figures 6A, 6B:
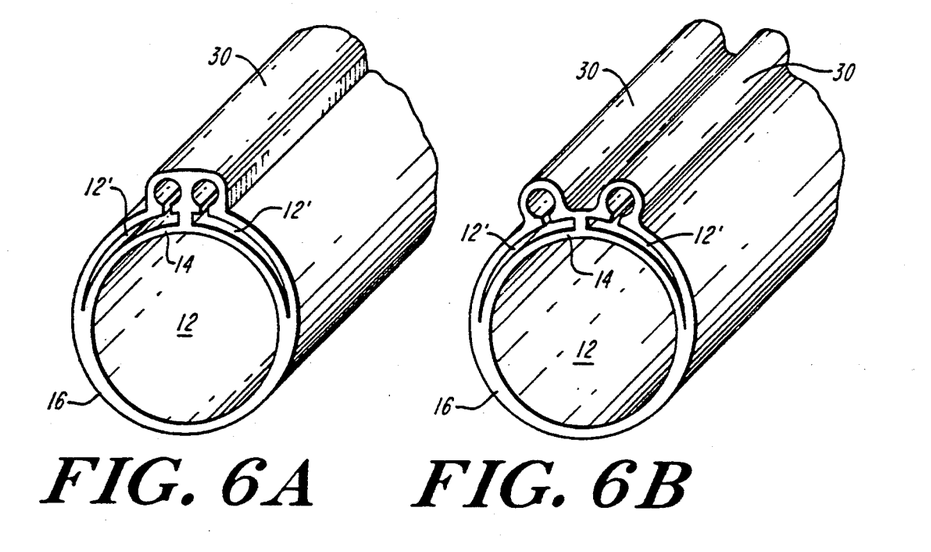
FIG. 6A is a schematic perspective view of an alternate multilumenal embodiment of the invention.
FIG. 6B is a schematic perspective view of an alternate configuration of the embodiment of FIG. 6A.

Alternate embodiments of the present invention are shown in FIGS. 6A and 6B. In those embodiments, the secondary lumina 12' form a raised platform 30 to facilitate subcutaneous needle access. Reservoirs 32 extend from the secondary lumina 12' along the sides of the first lumen 12 to provide a greater surface area for diffusion of the drug across the microporous, semi-permeable, wall 14. As shown in FIG. 6B, needle access ports 34 may be separated for extracutaneous identification of the individual secondary lumina. In this manner, separate drugs may be delivered to separate secondary lumina.

Figure 7:
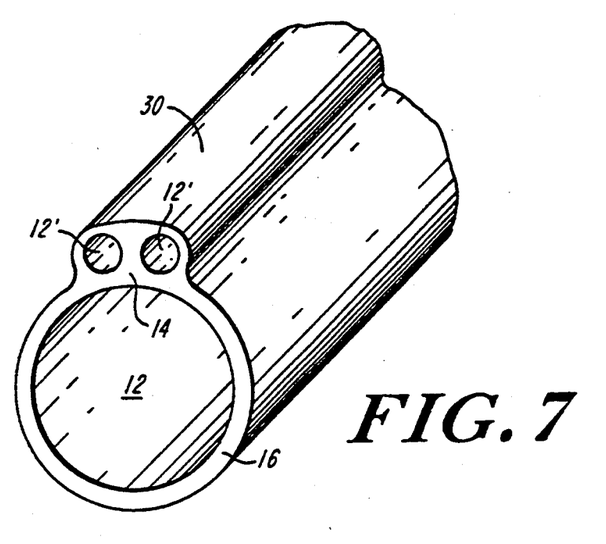
FIG. 7 is a schematic perspective view of an alternate configuration of the multilumenal embodiment of FIG. 6A.

Another embodiment of the prosthesis of the present invention is shown in FIG. 7, wherein needle access ports 34 are located in a single raised platform 30. In this illustrated embodiment, the secondary lumina 12' do not include reservoirs that extend along the sides of the first lumen 12. The secondary lumina of the illustrated embodiment extend either partially or fully along the length of the first lumen.

It should be understood that while several embodiments of the invention have been described in detail, the invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes coming within the meaning and range of equivalency of the claims are therefore intended to be embraced therein.

What is claimed is:

1. An implantable prosthetic device for sustained release of a bioactive material into a fluid flow pathway of a patient comprising a single tubular body extruded as a continuous wall, said wall having at least two interior lumina formed therein, said body being adapted for attachment to said fluid flow pathway, and said continuous wall defining
   (a) a primary lumen for accommodating fluid flow of said pathway
   (b) at least one secondary lumen being a space having an internal cross-dimension of at least 0.1 mm and located in said wall for receiving a quantity of bioactive material and extending adjacent said primary lumen, at least a portion of each said secondary lumen being separated from said primary lumen by a semipermeable membrane permitting controlled and sustained release of the bioactive material disposed in said lumen so as to allow the bioactive material to permeate from said secondary lumen through said membrane portion and into said primary lumen directly into the fluid flow pathway.

2. A device as set forth in claim 1 wherein said bioactive material is a therapeutic agent.

3. A device as set forth in claim 1 wherein said bioactive material is a diagnostic agent.

4. A device as set forth in claim 1 wherein said device is a vascular graft having said primary lumen disposed to form a blood flow pathway.

5. A device as set forth in claim 1 wherein said device is an organ graft having said primary lumen disposed to form an organ to organ fluid flow pathway.

6. The device of claim 1 wherein said body consists of polytetrafluoroethylene (PTFE).

7. The device of claim 6 wherein said polytetrafluoroethylene is selected from the group consisting of, expanded polytetrafluoroethylene, stretched polytetrafluoroethylene, and stretched and expanded polytetrafluoroethylene.

8. The device of claim 1 wherein said body consists of a material including copolymers.

9. An implantable prosthetic device for delivering a bioactive material into a blood vessel of a patient, the device comprising
   a single tubular body extruded as a continuous wall, said wall having at least two interior lumina formed therein and said body being adapted for attachment to a blood vessel of the patient, said lumina including
   (a) a primary lumen for accommodating blood flow therethrough along a blood flow path of said vessel, and
   (b) at least one secondary lumen for continuing a bioactive material at least a portion of which is separated from said primary lumen by a semipermeable membrane formed in said wall, said membrane being microporous permitting controlled and sustained release of the bioactive material and said at least one secondary lumen including a space having a cross-dimension of at least 0.1 mm and extending parallel to said primary lumen, said space being adapted to receive a supply of bioactive material for permeating through said microporous membrane into said primary lumen directly into the fluid flow pathway.

10. A device as set forth in claim 9 wherein said bioactive material is a therapeutic agent.

11. A device as set forth in claim 9 wherein said bioactive material is a diagnostic agent.

12. A device as set forth in claim 9 wherein said device is a vascular graft having said primary lumen disposed to form a blood flow pathway.

13. (Amended) A device as set forth in claim 9 wherein said device is an organ graft having said primary lumen disposed to form an organ to organ fluid flow pathway.

14. A device as set forth in claim 9 wherein said body consists of polytetrafluoroethylene.

15. The device of claim 14 wherein said polytetrafluoroethylene is selected from the group consisting of, expanded polytetrafluoroethylene, stretched polytetrafluoroethylene, and stretched and expanded polytetrafluoroethylene.

16. A device as set forth in claim 14 wherein said bioactive material is a therapeutic agent.

17. A device as set forth in claim 14 wherein said bioactive material is a diagnostic agent.

18. The device of claim 9 wherein said body consists of a material including copolymers.

19. An implantable prosthetic device for delivering a bioactive material into a blood vessel of a patient, the device comprising a single tubular body extruded as a continuous wall, said wall consisting of a polytetrafluoroethylene and formed as a continuous extrusion having at least two lumina formed therein including a primary lumen adapted for attachment to a blood vessel of the patient and a secondary lumen, (a) said primary lumen within said wall accommodating blood flow therethrough along a blood flow path of the vessel, and (b) said secondary lumen for containing a supply of bioactive material within said wall at least a portion of which is separated from said primary lumen by a semipermeable microporous membrane portion of said continuous wall permitting controlled and sustained release of the bioactive material, said secondary lumen having an internal cross dimension of between 0.1 and 6 millimeters being adapted for containing a supply of bioactive material, for permeating through said microporous membrane portion into said primary lumen into the fluid flow pathway.

20. The device of claim 19 wherein said wall is a polytetrafluoroethylene is selected from the group consisting of expanded polytetrafluoroethylene, stretched polytetrafluorothylene, and stretched and expanded polytetrafluoroethylene.

* * * * *

UNITED STATES PATENT AND TRADEMARK OFFICE
CERTIFICATE OF CORRECTION

PATENT NO. : 5,411,550
DATED : May 2, 1995
INVENTOR(S) : Steve A. Herweck, Theodore Karwoski, and Paul Martakos It is certified that error appears in the above-indentified patent and that said Letters Patent is hereby corrected as shown below:

Column 10, line 41 replace "12°" with --12'--.

Column 12, line 43 replace "continuing" with --containing--

Signed and Sealed this

Twenty-sixth Day of December, 1995

Attest:

BRUCE LEHMAN

*Attesting Officer*  *Commissioner of Patents and Trademarks*